(12) United States Patent
Umemoto et al.

(10) Patent No.: US 10,105,102 B2
(45) Date of Patent: Oct. 23, 2018

(54) PACKAGE FOR PROCESSING SENSED-DATA, SENSED-DATA PROCESSOR, AND SYSTEM FOR PROCESSING SENSED-DATA

(71) Applicant: Samsung Electronics Co., Ltd., Suwon-si, Gyeonggi-do (KR)

(72) Inventors: Mitsuo Umemoto, Seongnam-si (KR); Yung-Cheol Kong, Cheonan-si (KR); Woon-Bae Kim, Seoul (KR); Pyoung-Wan Kim, Suwon-si (KR); Kyong-Soon Cho, Incheon (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 587 days.

(21) Appl. No.: 14/703,833

(22) Filed: May 4, 2015

(65) Prior Publication Data

US 2016/0051197 A1 Feb. 25, 2016

(30) Foreign Application Priority Data

Aug. 20, 2014 (KR) .................. 10-2014-0108585

(51) Int. Cl.
*A61B 5/00* (2006.01)
*A61B 5/145* (2006.01)
*A61B 5/0215* (2006.01)

(52) U.S. Cl.
CPC .......... *A61B 5/6861* (2013.01); *A61B 5/0031* (2013.01); *A61B 5/0215* (2013.01); *A61B 5/14503* (2013.01); *A61B 5/14532* (2013.01); *A61B 2562/162* (2013.01); *A61B 2562/166* (2013.01)

(58) Field of Classification Search
CPC combination set(s) only.
See application file for complete search history.

(56) References Cited

U.S. PATENT DOCUMENTS

| 6,707,160 B2 | 3/2004 | Yamaji |
| 7,689,159 B2 | 3/2010 | Nojima |
| 7,916,013 B2 | 3/2011 | Stevenson |
| 8,253,555 B2 | 8/2012 | Stevenson et al. |

(Continued)

FOREIGN PATENT DOCUMENTS

JP 3265301 12/2001

OTHER PUBLICATIONS

Sekitani et al. ("Flexible organic transistors and circuits with extreme bending stability," Nature Materials, vol. 9, Dec. 2010).*

*Primary Examiner* — Scott T Luan
(74) *Attorney, Agent, or Firm* — Renaissance IP Law Group LLP

(57) ABSTRACT

Provided is a body-implantable package for processing biosensed-data for wireless communication to an external device. The package includes a tube closed by a cover, therein, a chip with a strained layer affixed thereto to form a flexible laminar circuit. The cover is fitted over an open end of the tube after the laminated chip and strained layer are inserted therein. The chip is constructed of and rolled in one or more turns into a generally cylindrical shape. The strained layer is affixed to a surface of the chip automatically to cause the flexible laminar circuit to curl into a generally cylindrical shape to fit within the tube.

10 Claims, 12 Drawing Sheets

(56) References Cited

U.S. PATENT DOCUMENTS

| | | |
|---|---|---|
| 8,680,688 B2 | 3/2014 | Kang et al. |
| 2003/0139778 A1* | 7/2003 | Fischell ............... A61B 5/0006 607/3 |
| 2012/0157804 A1 | 6/2012 | Rogers et al. |
| 2013/0076612 A1 | 3/2013 | Myers |
| 2013/0144379 A1* | 6/2013 | Najafi .................. A61B 5/0024 623/2.11 |
| 2013/0171490 A1 | 7/2013 | Rothkopf et al. |
| 2013/0273413 A1 | 10/2013 | Fahlgren et al. |
| 2014/0234977 A1* | 8/2014 | Grimm ............. H01L 29/66522 436/39 |

* cited by examiner

PACKAGE FOR PROCESSING SENSED-DATA, SENSED-DATA PROCESSOR, AND SYSTEM FOR PROCESSING SENSED-DATA

CROSS-REFERENCE TO RELATED APPLICATION

This application claims priority under 35 U.S.C. § 119 to Korean Patent Application No. 10-2014-0108585 filed on Aug. 20, 2014, the disclosure of which is hereby incorporated by reference in its entirety.

BACKGROUND

Field

Embodiments of the inventive concept relate to a package for processing sensed-data, a sensed-data processor, and a system for processing sensed-data.

Description of Related Art

As a method for testing symptoms or diseases in a human body, an in-vitro test performed by transferring a tissue out of the human body has been generally used. The in-vitro test includes a blood test, a tissue test, etc. In a case of a symptom requiring rapid sensing, a method in which a sensed-data processor is implanted into the human body to sense the symptom in real time is also used. A body-implantable package for processing sensed-data uses the implanted sensed-data processor. With the body-implantable package for processing the sensed-data, the package is implanted into the human body to sense a physiological change in the human body, for example an arrhythmia, blood pressure, blood sugar level, etc., and in real time to store the sensed-data in an internal memory or to transmit the sensed-data to an external device.

SUMMARY

Embodiments of the inventive concept provide a sensed-data processor capable of being easily inserted into a body-implantable tube.

Embodiments of the inventive concept also provide a sensed-data processor capable of decreasing a volume thereof as desired.

Embodiments of the inventive concept also provide a package for processing sensed-data that is capable of generating an analysis result.

The technical objectives of the inventive concept are not limited to the above disclosure; other objectives may become apparent to those of ordinary skill in the art based on the following descriptions.

The present inventive concept provides a body-implantable package for processing sensed-data, a sensed-data processor, and a system for processing sensed-data.

In accordance with an aspect of the inventive concept, a package for processing sensed-data may include a tube, a cover, a chip, and a strained layer.

The cover may be used to close an open end of the tube.

The chip may be installed in the tube.

The chip may be 'rolled up' in one or more turns into a generally cylindrical circuit.

The strained layer may be affixed to a surface of the chip.

In some embodiments, the package for processing the sensed-data may include a fixing part configured to fix a combined structure of the chip and the strained layer onto an inner surface of the tube. The chip and the strained layer may be spaced apart from the inner surface of the tube.

In other embodiments, the chip and the strained layer may be rolled up into circuit having the strained layer facing the interior thereof.

In still other embodiments, the chip may be rolled up into a circuit having the chip facing the interior thereof.

In yet other embodiments, the package may include a battery coupled to the chip.

In yet other embodiments, the package may include a sensor coupled to the chip.

In yet other embodiments, the chip may include a wireless communication circuit.

In yet other embodiments, the package may include a wireless communication part coupled to the chip.

In accordance with another aspect of the inventive concept, a sensed-data processor may include a chip and a strained layer.

The chip may be rolled up in one or more turns.

The strained layer may be affixed to a surface of the chip.

In some embodiments, a circuit layer of the chip may be affixed to the strained layer.

In other embodiments, a rear surface of the chip may be affixed to the strained layer.

In still other embodiments, the strained layer may include at least one selected from silicon oxide (SiO,) silicon hydroxide (SiOH), silicon nitride (SiN), silicon nitrate (SiON), silicon nitrene (SiHN), aluminum oxide (AlO), or zirconium oxide (ZrO), and the strained layer may have a thickness of about 1 to 3 micrometers (μm).

In yet other embodiments, the strained layer may include silicon (Si), and the strained layer may have a thickness of about 3 to 10 μm.

In yet other embodiments, the chip may have a thickness of about 3 to 10 μm.

In yet other embodiments, the chip may have a width and length of about 2 to 10 mm.

In yet other embodiments, the chip may include a system on ship (SoC).

In yet other embodiments, the chip may include a power generation part.

In accordance with another aspect of the inventive concept, a system for processing sensed-data may include a package for processing sensed-data and an external device.

The package for processing the sensed-data may include a tube, a cover, a chip, a strained layer, and a battery. The cover may be combined with the tube. The chip may be built in the tube. The chip may be rolled up in one or more turns. The chip may have a wireless communication circuit. The strained layer may be combined with a surface of the chip. The battery may be coupled to the chip.

The external device may be configured to wirelessly communicate with the package for processing the sensed-data.

In some embodiments, the system may include a repeater configured to relay a wireless signal from the package to the external device.

BRIEF DESCRIPTION OF THE DRAWINGS

The foregoing and other features and advantages of the inventive concepts will be apparent from the more particular description of preferred embodiments of the inventive concepts, as illustrated in the accompanying drawings in which like reference characters refer to the same parts throughout the different views. The drawings are not necessarily to scale, emphasis instead being placed upon illustrating the principles of the inventive concepts. In the drawings.

DETAILED DESCRIPTION OF THE EMBODIMENTS

Figure 1:
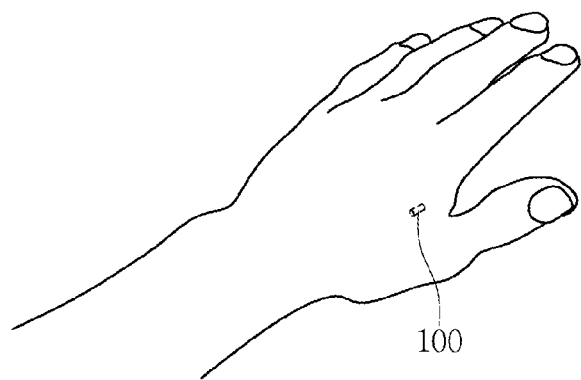
FIG. 1 is an application view of a body-implantable package for processing sensed-data in accordance with embodiments of the inventive concept.

Various embodiments will now be described more fully with reference to the accompanying drawings in which some embodiments are shown. These inventive concepts may, however, be embodied in different forms and should not be construed as limited to the embodiments set forth herein. Rather, these embodiments are provided so that this disclosure is thorough and complete and fully conveys the inventive concept to those skilled in the art.

In the embodiments, it will be understood that when an element is referred to as being "formed on" another element, it can be directly formed on the other element or intervening elements may be present. Also, in the drawings, the thicknesses of elements may be exaggerated for clarity and better understanding. Features within drawings may appear to be slightly deformed by dimensional manufacturing tolerances and/or another allowable error. The examples of the inventive concept are not limited to a predetermined shape, but include variations based on design choices and/or manufacturing processes. For example, a rectangular area may be rounded or curved at a predetermined curvature.

In the drawings, example areas have various properties including sizes and shapes. The shapes of the example areas are illustrated for predetermined shapes, but without any intended limitation. In other words, the shapes of the example areas are not intended to limit the scope of the inventive concept. It will be understood that, although the terms first, second, etc. may be used herein to describe various elements, the elements should not be limited by these terms. These terms are only used to distinguish one element from another element. The examples illustrated herein include complementary examples wherein, for example, elements may be swapped with one another.

The terminology used herein is for the purpose of describing particular embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, a word "strained" is intended to include both shrinkage and expansion. It will be further understood upon a full and fair reading of the context and structure of the various embodiments that the term "tensile" means nominally expansive but having a tendency to shrink and bend inwardly, and the term "compressive" means nominally contracted or compressed but having a tendency to expand and bend outwardly.

Hereinafter, embodiments of the inventive concept will be described in detail with reference to the accompanying drawings.

FIG. 1 is an application view of a body-implantable package for processing sensed-data in accordance with embodiments of the inventive concept.

Referring to FIG. 1, the body-implantable package 100 for processing the sensed-data may be implanted into a muscle of a hand. The body-implantable package 100 for processing the sensed-data may be implanted into various portions of a human body. For example, the body-implantable package 100 for processing the sensed-data may be implanted into a muscle adjacent to a heart, for example, a pectoral muscle near an armpit, to sense heart rates. The body-implantable package 100 for processing the sensed-data may be implanted in or along digestive organs such as a stomach, a small intestine, a large intestine, etc., using an endoscope capsule.

The body-implantable package 100 for processing the sensed-data may be implanted into a human body to sense a physiological change of the human body, for example, a blood pressure, blood sugar, a heart rate, etc., to performing signal processing on the sensed-data and to transmit the processed data to an external device for storing, forwarding, and/or analysis.

The body-implantable package 100 for processing the sensed-data may be implanted using a syringe, or an incision may be needed.

The body-implantable package 100 for processing the sensed-data may have various sizes that require various implantation techniques.

Figure 2:
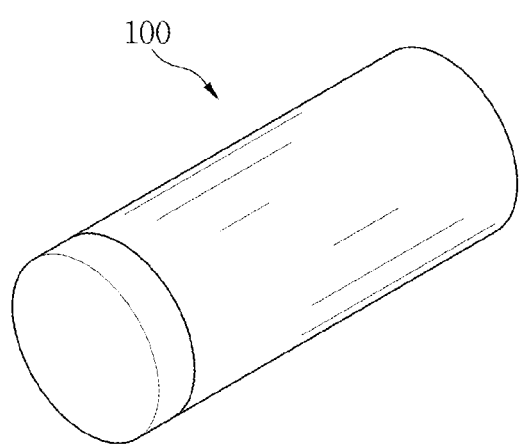
FIG. 2 is an isometric view of a body-implantable package for processing sensed-data in accordance with embodiments of the inventive concept.
Figure 3:
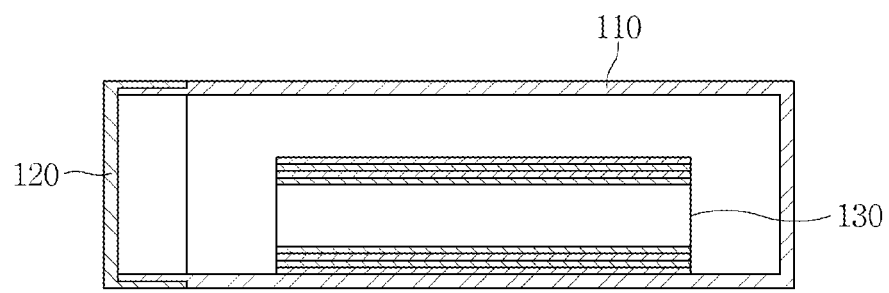
FIG. 3 is a cross-sectional view of a body-implantable package for processing sensed-data in accordance with embodiments of the inventive concept.

FIG. 2 is an isometric view of a body-implantable package for processing sensed-data in accordance with embodiments of the inventive concept. FIG. 3 is a cross-sectional view of a body-implantable package for processing sensed-data in accordance with embodiments of the inventive concept.

Referring to FIG. 2, the body-implantable package 100 for processing the sensed-data may have a cylindrical shape. The body-implantable package 100 for processing the sensed-data may have an open but close-able end, a cylindrical inner space and a circular cross section. In FIG. 2, the body-implantable package 100 for processing the sensed-data has circularly cross-sectional cylindrical shape. Alternatively, the body-implantable package 100 for processing the sensed-data may have various shapes such as an oval cylindrical shape, a triangular shape, a quadrangular shape, a pentagonal shape, etc.

Referring to FIG. 3, the body-implantable package 100 for processing the sensed-data may include an open-ended tube 110, a cover 120, a sensed-data processor 130, etc.

The sensed-data processor 130 may be disposed inside the tube 110. The tube 110 may have a circular or oval cylindrical shape. When the tube 110 has the cylindrical shape, the sensed-data processor 130 that is rolled up as a cylindrical cross-section may be easily inserted into the tube 110. Alternatively, the tube 110 may have a triangular shape, a quadrangular shape, a pentagonal shape, etc. The tube 110 may have a closed end and an open end that is disposed opposite to the closed end. Alternatively, the tube 110 may have both ends that are open. When both ends of the tube 110 are open, two covers 120 may be combined with the two open ends of the tube 110 to close the ends.

The tube 110 may be rigid or flexible. For example, a rigid tube 110 may be made of or at least may include glass, ceramic, etc. Alternatively, a flexible tube 110 may be made of or at least may include a polyurethane-based resin such as Estane, Pellethane, Carbothane, Tecoflex, Techothane, Texin, etc., a nylon-based resin such as Aesno, Besno, nylon 6, nylon 6.6, Pebax, Vestamid, etc., or silicone, etc.

The cover 120 is used with the tube 110 to close the open end of the tube 110. After the sensed-data processor 130 is inserted into the tube 110, the cover 120 is fitted over an outer surface of the open end of the tube 110 to form a planar closure surface. When the tube 110 has two open ends, two covers 120 may be used to close the two open ends of the tube 110.

The cover 120 also may be rigid or flexible. The cover 120 may be made of or at least may include substantially the same or similar material as the tube 110. When the tube 110 is rigid, the cover 120 may be rigid or flexible. When the tube 110 is flexible, the cover 120 may be rigid. The tube 110 may be joined with the cover 120 using a joint compound or other suitable combining member, for example, an adhesive, gold brazing, etc.

The sensed-data processor 130 may be rolled into a generally cylindrically shaped circuit. The sensed-data processor 130 may be inserted into the tube 110. When a greater number of tighter rolled turns is used, the volume of the sensed-data processor 130 may be decreased.

In FIG. 3, when a diameter of the sensed-data processor 130 is smaller than an inside diameter of the tube 110, the sensed-data processor 130 may drift in the tube 110. When the diameter of the sensed-data processor 130 is substantially the same as the internal diameter of the tube 110, the sensed-data processor 130 may be installed inside the tube 110 so that the outer generally cylindrical surface of the sensed-data processor 130 comes in contact with the inner cylindrical surface of the tube 110. Although the diameter of the sensed-data processor 130 may be greater than the internal diameter of the tube 110, the sensed-data processor 130 is flexible enough to have a shrinkable diameter in a radial direction so that the outer surface of the sensed-data processor 130 may be inserted within the tube 110 such that the outer generally cylindrical surface of the diametrically-reduced sensed-data processor 130 comes in contact with the inner cylindrical surface of the tube 110.

The sensed-data processor 130 may include a system on chip (SoC). Thus, the sensed-data processor 130 may be configured to be of chip size. The sensed-data processor 130 may have a width and length of about 2 to 10 mm.

The sensed-data processor 130 may include a microprocessor that performs signal processing on the sensed result to generate new information. For example, a microprocessor could process cardiac sensed waveform data to derive QRS and other significant peak amplitude information therefrom.

The sensed-data processor 130 may include a power generation part that generates a power based on an electromagnetic wave that is received from an external device.

The sensed-data processor 130 may include a wireless communication part that wirelessly transmits the signal-processed result to the external device.

Figure 4:
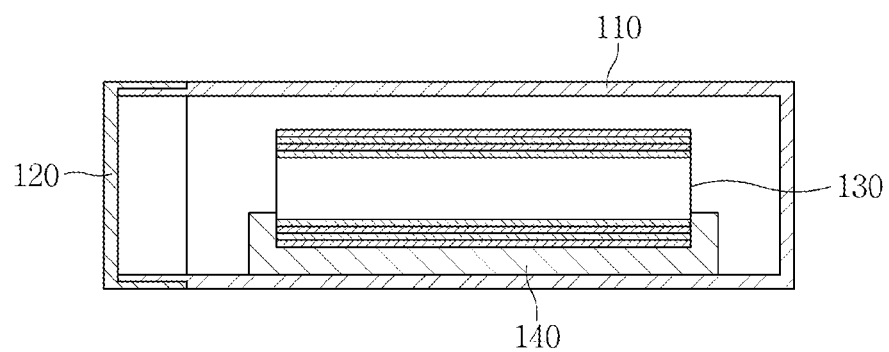
FIG. 4 is a cross-sectional view of a variation of the body-implantable package for processing the sensed-data shown in FIG. 3.

FIG. 4 is a cross-sectional view of a variation of the body-implantable package for processing the sensed-data shown in FIG. 3.

Referring to FIG. 4, the body-implantable package 100 for processing the sensed-data may include a fixing part 140 that anchors or fixes a sensed-data processor 130 in a desired position and orientation inside of the tube 110. One side of the fixing part 140 may be affixed to the sensed-data processor 130, and another side of the fixing part 140 may be affixed to an inner surface, e.g. an inner sidewall, of the tube 110. As shown in FIG. 4, the fixing part 140 may be affixed to an outer surface of the sensed-data processor 130 and an inner surface of the tube 110. alternatively, the fixing part 140 may be affixed to an outer surface of an end portion of the sensed-data processor 130 in a longitudinal direction and an inner surface of an end portion of the tube 110 in the longitudinal direction. With the fixing part 140 formed on the inner surface of the tube 110, the sensed-data processor 130 may be spaced apart from the inner surface of the tube 110.

The fixing part 140 may include a non-conductive material such as a non-conductive epoxy of a thermosetting resin, silicone, etc. (since the fixing part 140 is disposed and may be sealingly enclosed within the closed tube 110, the fixing part 140 may include a toxic or a bio-incompatible material, without risk of injury to or contamination of a human body into which body-implantable package 100 is implanted.)

Figure 5:
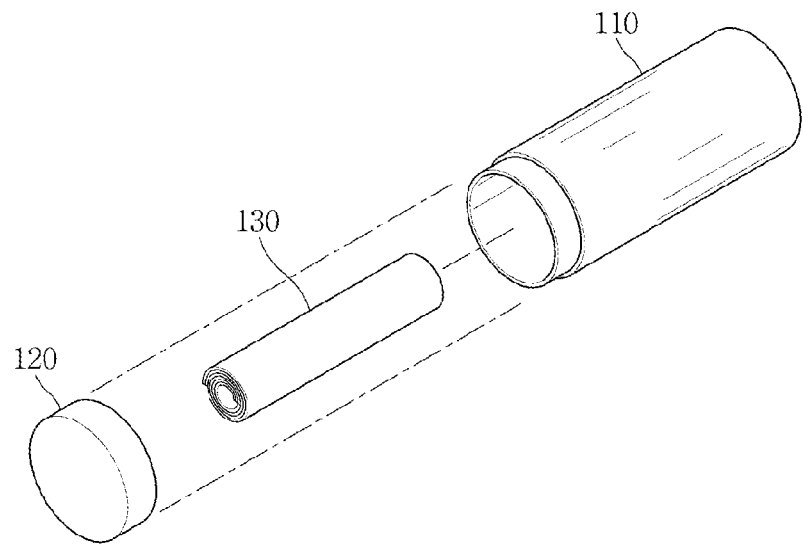
FIG. 5 is an exploded isometric view of the body-implantable package for processing the sensed-data shown in FIG. 3.

FIG. 5 is an exploded isometric view of the body-implantable package for processing the sensed-data shown in FIG. 3.

Referring to FIG. 5, the sensed-data processor 130 is inserted into the tube 110. The cover 120 is fitted on a normally open end of the tube 110 to close the tube 110. Thus, the body-implantable package 100 for processing the sensed-data is ready to implant.

Figure 6:
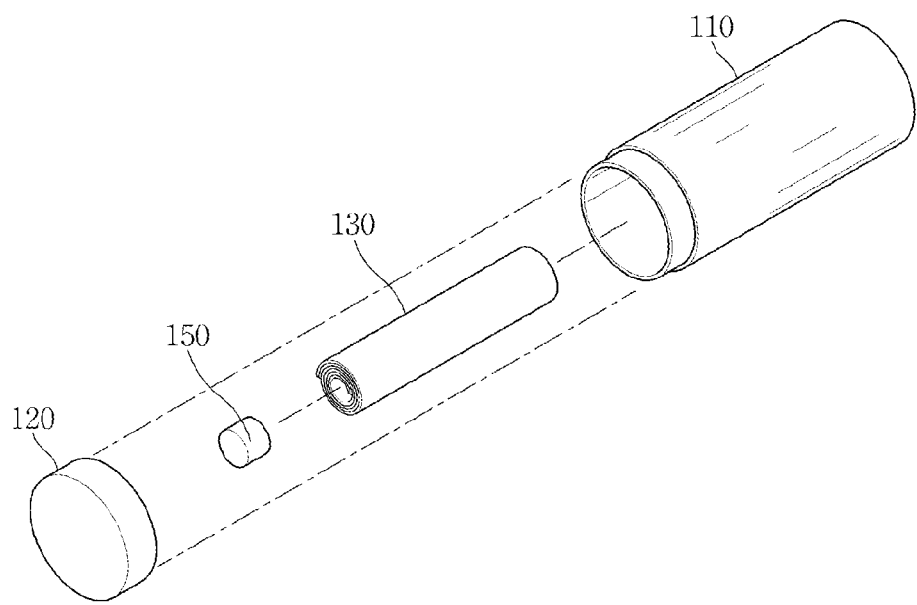
FIG. 6 is an exploded isometric view of a variation of the body-implantable package for processing the sensed-data shown in FIG. 3.

FIG. 6 is an exploded isometric view of a variation of the body-implantable package for processing the sensed-data shown in FIG. 3.

Referring to FIG. 6, the body-implantable package 100 for processing the sensed-data may include an auxiliary element 150. The auxiliary element 150 may be coupled to the sensed-data processor 130.

The auxiliary element 150 may include a battery. When the sensed-data processor 130 does not include a power generation part, the body-implantable package 100 for processing the sensed-data may instead include the battery. The battery provides an electric power to the sensed-data processor 130. however, when the battery is depleted, the sensed-data processor 130 may cease operation. Even though the sensed-data processor 130 includes the power generation part, the body-implantable package 100 for processing the sensed-data may also include the battery as the auxiliary element 150.

The auxiliary element 150 may include a sensor. The sensor senses a physiological change in a human body. The sensor may be a blood pressure sensor, a heart rate sensor, a camera, a thermometer, a composition detection sensor, etc. The auxiliary element 150 may include a single sensor. Alternatively, the auxiliary element 150 may include a multiplicity or plurality of sensors. The sensors may transmit the sensed signal to the sensed-data processor 130. Even though the sensed-data processor 130 includes a sensor, the body-implantable package 100 for processing the sensed-data may include an additional sensor within the auxiliary element 150 to enhance sensing capability.

The auxiliary element 150 may include a wireless communication part. The wireless communication part may include a wireless communication circuit, an antenna, etc. Alternatively, the wireless communication part may include only an antenna. When the sensed-data processor 130 does not include the wireless communication circuit, the body-implantable package 100 for processing the sensed-data nevertheless may include a wireless communication part to communicate with an external device. Even though the sensed-data processor 130 includes the wireless communication part, the antenna may be disposed not in the sensed-data processor 130 but instead in the auxiliary element 150.

The auxiliary element 150 may include elements other than the battery, the sensor, and the wireless communication part. For example, the auxiliary element 150 may include a drug tube. The drug tube, for example, may include insulin to be used by a diabetic. The drug tube may be configured to be destroyed by the sensed-data processor 130. The drug may include a solvent that is capable of dissolving the material from which the tube 110 is made as well as the insulin normally sealingly contained therein. When the drug tube is destroyed, a portion of the tube 110 is dissolved to form a through hole and then the insulin is injected into the human body through the hole.

The auxiliary element 150 may include a combination of functional elements including at least two of the battery, the sensor, the wireless communication part, etc. The auxiliary element 150 may have various structures to perform a desired function of the sensed-data processor 130 and/or other required functions.

Figure 7:
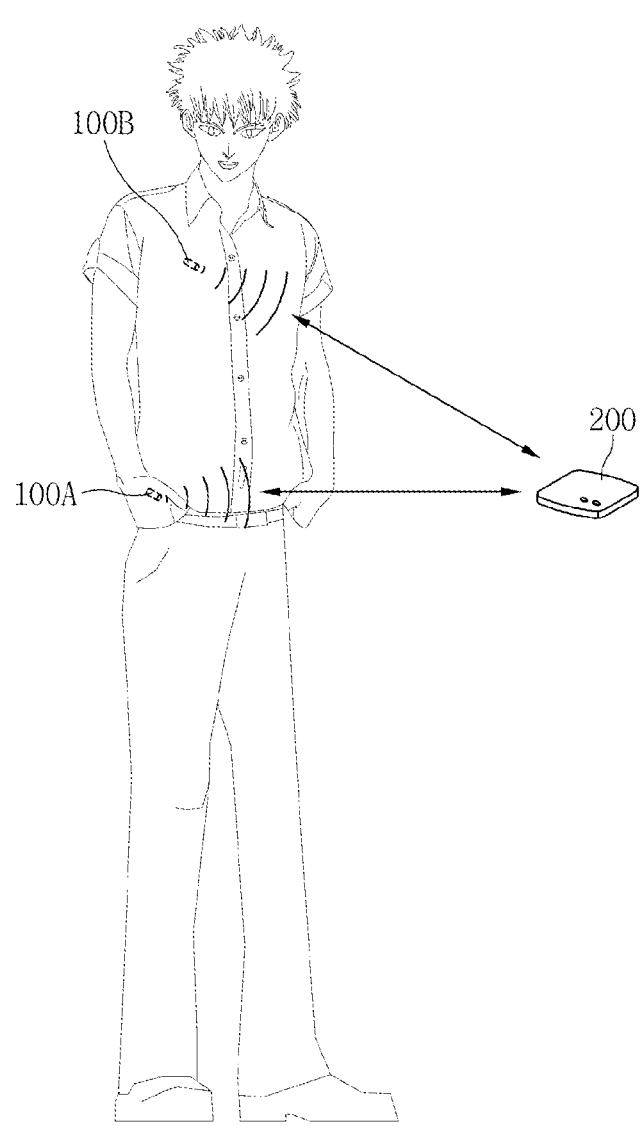
FIG. 7 is an application view of a system for processing sensed-data in accordance with embodiments of the inventive concept.

FIG. 7 is an application view of a system for processing sensed-data in accordance with embodiments of the inventive concept.

Referring to FIG. 7, the system for processing the sensed-data includes a plurality of body-implantable packages 100A and 100B for processing the sensed-data, an external device 200, etc.

The plurality of the body-implantable packages 100A and 100B for processing the sensed-data may be implanted into a human body. For example, a first body-implantable package 100A for processing the sensed-data senses a blood pressure of the human body, and a second body-implantable package 100B for processing the sensed-data senses a heart rate of the human body.

The body-implantable packages 100A and 100B for processing the sensed-data may wirelessly transmit sensed-and-processed data to the external device 200.

The external device 200 wirelessly receives the sensed-and-processed-data signal from the body-implantable packages 100A and 100B. Device 200 then analyzes, stores, forwards, and/or performs a corresponding process, etc., on the sensed-and-processed data signal.

The external device 200 may include a transmitter/receiver (transceiver) part, a database, a cell phone, a sensed signal analyzing part, a control part, a display, etc.

The transceiver part includes an antenna, a wireless communication circuit, etc. The transceiver part receives the sensed signal from the body-implantable packages 100A and 100B for processing the sensed-data to transmit the sensed signal to the sensed signal analyzing part. The transceiver part may transmit data or a command to the body-implantable packages 100A and 100B for processing the sensed-data.

The database may store the sensed signal received from the body-implantable packages 100A and 100B for processing the sensed-data, analysis information generated by the sensed signal analyzing part, reference information for analyzing the sensed signal, individual information, etc. The individual information may include a subject's, e.g. a patient's, information such as a name, a birth date, an address, and/or a cell phone number, etc. The individual information may include a guardian's information such as a cell phone number, etc. The individual information may include information regarding a patient's doctor, for example, and/or other primary care physician's or clinic's cell phone number, etc.

The sensed signal analyzing part analyzes the sensed signal that is received from the body-implantable packages 100A and 100B for processing the sensed-data to generate analysis information. For example, when the sensed signal analyzing part receives a sensed signal of a blood pressure from the body-implantable packages 100A and 100B for processing the sensed-data, the sensed signal analyzing part decides whether the sensed signal of the blood pressure is greater than a reference, e.g. one representing a danger or warning level, blood pressure. When the sensed signal of the blood pressure is greater than the reference blood pressure, the sensed signal analyzing part may generate an abnormal blood pressure signal.

The control part may transmit the sensed signal to the sensed signal analyzing part, which is received from the body-implantable packages 100A and 100B for processing the sensed-data by the transceiver part. When the sensed signal analyzing part generates the warning signal such as the out-of-bounds blood pressure signal, the control part may store the warning signal and may transmit a warning message or alarm corresponding to the abnormal blood pressure signal to a cell phone of the patient, the guardian, the doctor, and/or the clinic, etc.

The display may display the sensed signal, the analyzed information, the warning message, etc., in real time, during a predetermined time period, and/or by a predetermined manipulation.

The external device 200 may be coupled to a telecommunication company to receive location data of the patient, etc. The external device 200 may transmit the status data of the patient, location data of the patient, etc., to a nearby emergency center.

Figure 8:
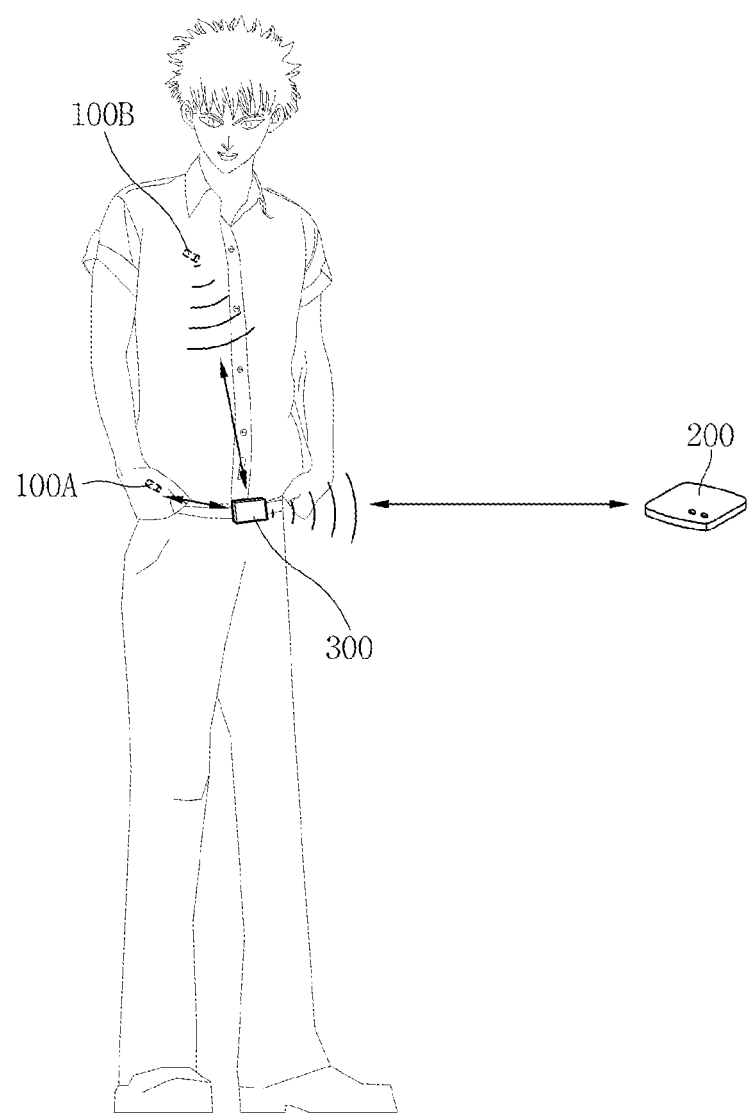
FIG. 8 is an application view of a variation of the system for processing the sensed-data shown in FIG. 7.

FIG. 8 is an application view of a variation of the system for processing the sensed-data shown in FIG. 7.

Referring to FIG. 8, the system for processing the sensed-data may include a repeater 300 that receives the sensed signal from the body-implantable packages 100A and 100B for processing the sensed-data to the external device 200. The repeater 300 may include a transceiver part, a control part, and/or a battery, etc. The repeater 300 may be disposed on an external region of a human body or clothes worn thereon. For example, repeater 300 may be attached to an outer surface of the human body or on an exterior clothing region or accessory, e.g. a belt.

The repeater 300 may include a memory. The memory of the repeater 300 may store identification information of the body-implantable packages 100A and 100B and/or identification information of the external device 200, etc. When the repeater 300 receives the sensed signal from the body-implantable packages 100A and 100B, the repeater 300 checks whether the identification information of the body-implantable packages 100A and 100B, which is received with the sensed signal, is stored in the memory. When the identification information of the body-implantable packages 100A and 100B is stored in the memory of the repeater 300, the repeater 300 may transmit the sensed signal corresponding to the identification information to the external device 200 along with the sensed-data from the body-implantable packages 100A and 100B.

Figure 9:
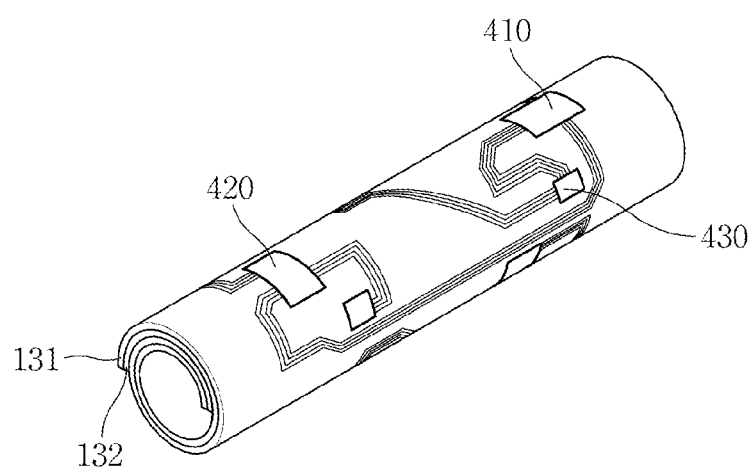
FIG. 9 is an isometric view of a sensed-data processor in accordance with an embodiment of the inventive concept.

FIG. 9 is an isometric view of a sensed-data processor in accordance with an embodiment of the inventive concept.

Referring to FIG. 9, the sensed-data processor may include a chip 131 and a strained layer 132. As shown in FIG. 9, the sensed-data processor may include the chip 131 integrally formed with the strained layer 132 that is formed on a rear surface of the chip 131. The sensed-data processor may have various sizes in a range of about 2 to about 10 mm of width (outside diameter) and length. Typically, it will be appreciated that sensed data processor is elongate or tubular in shape and has a larger length than diameter, as illustrated herein.

The chip 131 may include a system on chip (SoC). The chip 131 may include a main control part 410, a power generation part 420, and a wireless communication part 430. The chip 131 may further include a memory, an image processing part, a sensor part, etc.

The chip 131 may have a thickness suitable for ease of rolling it into a tubular shape. For example, the chip 131 may have a thickness of about 3 micrometers (μm) to about 10 μm. The number of the full circular rolls or turns of the chip 131 may be determined by an amount of expansion or shrinkage of the strained layer 132 that may be affixed to surface of the chip 131. In order to increase the number of the full rolls or turns of the chip 131, while maintaining a relatively small tube size suitable for insertion into the implantable tube 110 of body-implantable package 100, the chip 131 may have a thickness of about 2 μm to about 5 μm.

The strained layer 132 may be attached to the rear side of the chip 131. The strained layer 132 may be tensile (shrinkable) so that the strained layer 132 causes the attached chip 131 to curl inwardly toward the shrinking strained layer 132. When the strained layer 132 is rolled in such a direction that it is at the interior of the roll, the chip 131 combined with the strained layer 132 also rolled in the same direction. As shown in FIG. 9, the strained layer 132 may be rolled up in one or more turns.

The strained layer 132 may include silicon dioxide ($SiO_2$), SiOH, etc. A coefficient of thermal expansion (CTE) of $SiO_2$ and SiOH may be about $0.3 \times 10^{-6}$, and a modulus of elasticity of $SiO_2$ and SiOH may be about 70 gigapascals (GPa) to about 80 GPa. The strained layer 132 including $SiO_2$, SiOH may have a thickness of about 1 μm to about 3 μm. $SiO_2$, SiOH may be formed on a surface on which a circuit of the chip is formed or may be formed on a so-called 'rear' surface that is opposite to the circuit surface.

The strained layer 132 may include Si. A coefficient of thermal expansion (CTE) of Si may be about $2.4 \times 10^{-6}$, and a modulus of elasticity of Si may be about 185 GPa. The strained layer 132 including Si may have a thickness of about 3 μm to about 10 μm. Si may be formed on the surface on which the circuit of the chip is formed or it may be formed on the opposite, so-called 'rear' surface to the surface on which the circuit is formed.

The strained layer 132 may include trisilicon tetranitride ($Si_3N_4$), SiON, SiHN, etc. A coefficient of thermal expansion (CTE) of $Si_3N_4$, SiON, SiHN may be about $3.0 \times 10^{-6}$ to about $3.5 \times 10^{-6}$, and a modulus of elasticity of $Si_3N_4$, SiON, SiHN may be about 240 GPa to about 300 GPa. The strained layer 132 including $Si_3N_4$, SiON, SiHN may have a thickness of about 1 μm to about 3 μm. $Si_3N_4$, SiON, SiHN may be coated on the rear surface of the chip 131. Alternatively, $Si_3N_4$, SiON, SiHN may be coated on the surface on which the circuit of the chip is formed.

The strained layer 132 may include aluminum oxide ($Al_2O_3$). A coefficient of thermal expansion (CTE) of $Al_2O_3$ may be about $5.0 \times 10^{-6}$ to $7.0 \times 10^{-6}$, and a modulus of elasticity of $Al_2O_3$ may be about 380 GPa to about 400 GPa. The strained layer 132 including $Al_2O_3$ may have a thickness of about 1 μm to about 3 μm. $Al_2O_3$ may be coated on the rear surface of the chip 131. Alternatively, the surface on which the circuit of the chip is formed may be coated with $Al_2O_3$.

The strained layer 132 may include zirconium dioxide ($ZrO_2$). A coefficient of thermal expansion (CTE) of $ZrO_2$ may be about $9.0 \times 10^{-6}$ to $10.5 \times 10^{-6}$, and a modulus of elasticity of $ZrO_2$ may be about 250 GPa to about 300 GPa. The strained layer 132 including $ZrO_2$ may have a thickness of about 1 μm to about 3 μm. $ZrO_2$ may be coated on the rear surface of the chip 131. Alternatively, the surface on which the circuit of the chip is formed may be coated with $ZrO_2$.

Figure 10:
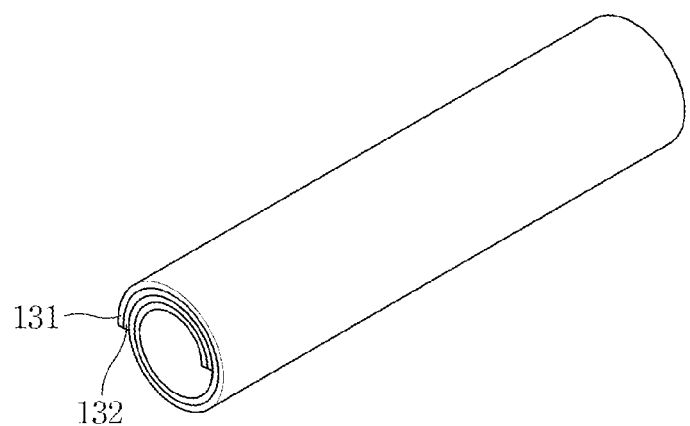
FIG. 10 is an isometric view of a variation of the sensed-data processor shown in FIG. 9.

FIG. 10 is an isometric view of a variation of the sensed-data processor shown in FIG. 9.

Referring to FIG. 10, the sensed-data processor may include a chip 131 and a strained layer 132. In the sensed-data processor shown in FIG. 10, the strained layer 132 is combined with a surface having a circuit layer of the chip 131 in a different way from the combination shown in FIG. 9. When a surface having a circuit layer of the chip 131 is coated with the strained layer 132, the surface having the circuit layer of the chip 131 may be protected.

The sensed-data processor shown in FIG. 10 is substantially the same as shown in FIG. 9. Thus, any repetitive explanations concerning the same elements will be omitted.

Figure 11:
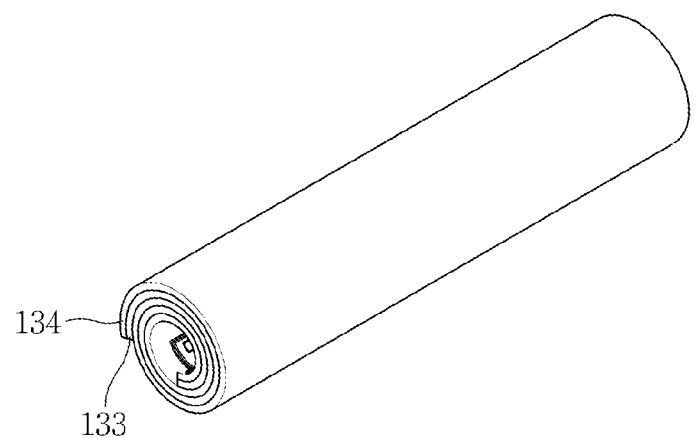
FIG. 11 is an isometric view of a sensed-data processor in accordance with another embodiment of the inventive concept.

FIG. 11 is an isometric view of a sensed-data processor in accordance with another embodiment of the inventive concept.

Referring to FIG. 11, the sensed-data processor may include a chip 133 and a strained layer 134. In the sensed-data processor shown in FIG. 11, the chip 133 is affixed to the strained layer 134 that is disposed on a rear surface of the chip 133 to form the sensed-data processor.

The chip 133 may include a system on chip (SoC). The chip 133 may include the chip 131 shown in FIG. 9, a main control part, a power generation part, a wireless communication circuit, a memory, an image processing part, etc. When the sensed-data processor is rolled by one or more turns into a generally cylindrical shape, a surface having a circuit layer of the chip 133 is disposed inside or toward the interior of the sensed-data processor. When the chip 133 is disposed inside the sensed-data processor, a sensor part may not operate well. Nevertheless, the chip 133 may include the sensor part disposed inside of the sensed-data processor.

In FIG. 11, the chip 133 may be rolled into a generally cylindrical shape in two or more turns. The number of rolls or turns of the chip 133 is determined by an amount of shrinkage or expansion of the strained layer 134 combined with the chip 133, a thickness of the chip 133, etc. For example, the chip 133 may have a thickness of about 3 μm to 10 μm to be easily rolled. Alternatively, the chip 133 may have a thickness of about 2 μm to 5 μm to be easily rolled into a generally cylindrical shape in no less than two turns.

As shown in FIG. 11, the strained layer 134 may be attached to the rear surface of the chip 133. The strained layer 132 may be compressible (expandable) so that the strained layer 132 causes the attached chip 131 to curl outwardly away from the shrinking strained layer 132. When the strained layer 134 is rolled toward the chip 133 such that the chip 133 is on the interior of the generally cylindrical roll, the chip 133 attached to the strained layer 134 rolls in the same direction. A surface having a circuit layer of the chip 133 (featured toward the end and toward the center of the roll in FIG. 11) may be exposed in an interior region of the sensed-data processor.

In FIG. 11, the strained layer 134 may be expandable. The expandable property of the strained layer 134 may be formed by a manufacturing technique using SiO, Si, SiOH, SiN, SiON, SiHN, AlO, ZrO, etc., and/or another material. The strained layer 134 may be rolled in one turn or more.

Figure 12:
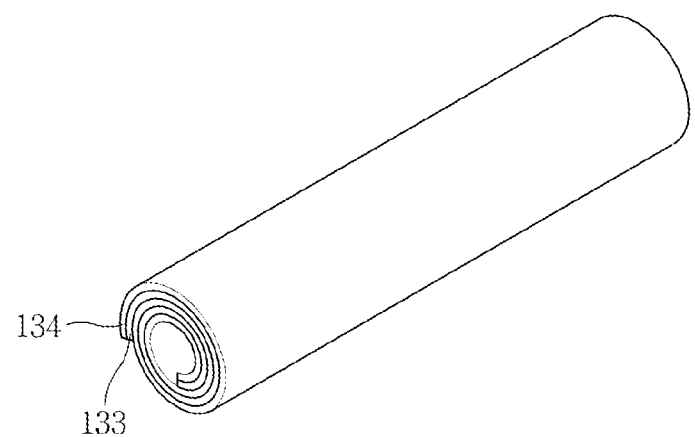
FIG. 12 is an isometric view of a variation of the sensed-data processor shown in FIG. 11.

FIG. 12 is an isometric view of a variation of the sensed-data processor shown in FIG. 11.

Referring to FIG. 12, the sensed-data processor may include a chip 133 and a strained layer 134. The sensed-data processor shown in FIG. 12 is substantially the same as shown in FIG. 11 except that a surface having a circuit layer of the chip 133 is attached to the strained layer 134. When the surface having the circuit layer of the chip 133 is coated with the strained layer 134, the strained layer 134 may be seen (by contrasting FIGS. 11 and 12) effectively to protect the surface of the chip 133 having the circuit layer.

FIGS. 13 to 22 are isometric views of successive steps a process of manufacturing a sensed-data processor in accordance with embodiments of the inventive concept.

Figure 13:
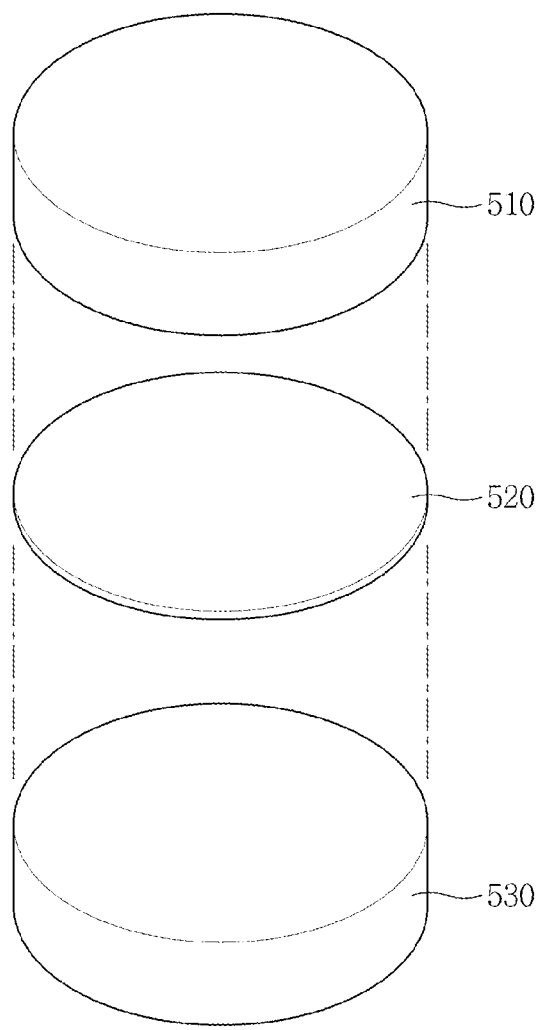
FIG. 13 is an isometric view of a first operation for manufacturing a sensed-data processor in accordance with embodiments of the inventive concept.

FIG. 13 is an isometric view of a first manufacturing step for manufacturing the sensed-data processor in accordance with embodiments of the inventive concept.

Referring to FIG. 13, in the first step, a device wafer 510, a tape 520, and a support substrate 530 may be prepared.

The device wafer 510 includes a plurality of chips such as a SoC that are formed on one surface thereof through a deposition process, an etching process, etc. The chips of the device wafer 510 may be separated through a dicing process in subsequent process steps.

The tape 520 fixes the device wafer 510 to the support substrate 530. The tape 520 may be adhesive. The tape 520 may include a material that is removable in a subsequent process. For example, the tape 520 may include a heat-responsive material that may be melted by heat, an ultraviolet-responsive material that may be melted by ultraviolet light, etc. The tape 520 may include a double-sided tape.

The support substrate 530 may support one surface of the device wafer 510 using the tape 520. The support substrate 530 may be made of or at least may any suitable material such as glass, silicon, and/or a ceramic, etc.

Figure 14:
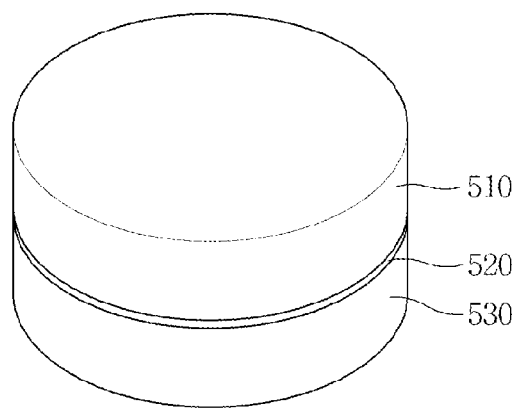
FIG. 14 is an isometric view of a second operation for manufacturing a sensed-data processor in accordance with embodiments of the inventive concept.

FIG. 14 is an isometric view of a second operation for manufacturing the sensed-data processor in accordance with embodiments of the inventive concept.

Referring to FIG. 14, in the second process step, the device wafer 510 is fixed to the support substrate 530 using the tape 520.

A rear (upper in FIGS. 13 and 14) surface of the device wafer 510 may be open, and a surface having a circuit layer may be attached to the tape 520.

Figure 15:
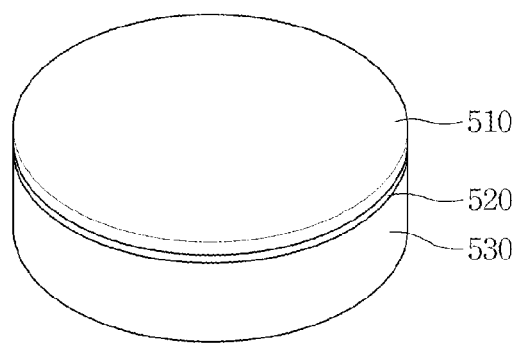
FIG. 15 is an isometric view of a third operation for manufacturing a sensed-data processor in accordance with embodiments of the inventive concept.

FIG. 15 is an isometric view of a third process step for manufacturing the sensed-data processor in accordance with embodiments of the inventive concept.

Referring to FIG. 15, in the third step, the rear surface of the device wafer 510 is grinded to decrease the thickness of the device wafer 510. The surface having the circuit layer of the device wafer 510 may be attached to the support substrate 530 using the tape 520 so that the device wafer 510 may be disposed on a turntable of a grinding apparatus. The rear surface of the device wafer 510 faces an upper side of the turntable. A grinding head, for example, a diamond wheel, is downwardly transported to press against the rear surface of the device wafer 510. A plurality of spindles may be attached to the grinding head. The spindles may be connected to a motor shaft. The grinding head may rotate by the rotation of the spindles. The turntable that holds the device wafer 510 may also be rotatable.

The grinding apparatus may include one or more grinding heads. For example, the grinding apparatus may include a first grinding head (for example, about 350 mesh) having a coarse surface, a second grinding head (for example, about 2,000 mesh) having a finer surface than that of the first grinding head, etc. After the thickness of the device wafer 510 is decreased by the first grinding head by a predetermined amount, minute cracks formed on the rear surface of the device wafer 510 may be removed by the second grinding head. Thus, the device wafer 510 may be grinded to a desired thickness, for example, about 3 μm to 10 μm.

Figure 16:
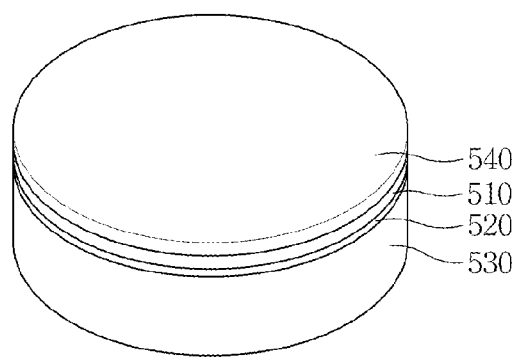
FIG. 16 is an isometric view of a fourth operation for manufacturing a sensed-data processor in accordance with embodiments of the inventive concept.

FIG. 16 is an isometric view of a fourth process step for manufacturing the sensed-data processor in accordance with embodiments of the inventive concept.

Referring to FIG. 16, in the fourth step, a strained layer 540 may be formed on the rear surface of the device wafer 510.

The strained layer 540 may include $SiO_2$, SiOH, $Si_3N_4$, SiON, SiHN, $Al_2O_3$, $ZrO_2$, etc., and the strained layer 540 may be formed through physical vapor deposition (PVD), chemical vapor deposition (CVD), spin coating, etc. SiO2, SiOH, $Si_3N_4$, SiON, SiHN, $Al_2O_3$, $ZrO_2$, etc., may be deposited at a temperature of about 180 to about 320 to form the strained layer 540 in a thin film. The strained layer 540 may have a thickness of about 1 μm to about 3 μm.

The strained layer 540 may be formed through the physical vapor deposition (PVD), the chemical vapor deposition (CVD), the spin coating, etc., using Si. The strained layer 540 having Si may be deposited at a temperature of about 180 to about 320 to form the strained layer 540 in a thin film. The strained layer 540 having Si may have a thickness of about 3 µm to about 10 µm.

Those of skill in the art will appreciate that the affixing of a flexible nominally planar strained layer to a substantially congruent or coextensive flexible nominally planar circuit layer in the manner described and illustrated herein curl-biases the resulting laminar and flexible circuit structure to roll into a generally cylindrical shape. The curl-bias direction of course depends upon whether the strained layer is tensile or compressive as defined herein. Thus, individual laminar flexible circuit structures automatically roll in one or more turns into generally cylindrical shapes when they are individuated by the processes to be described immediately below, whereby they are individuated by a dicing process step and are further separated from the substrate by a melting process step now to be described.

Figure 17:
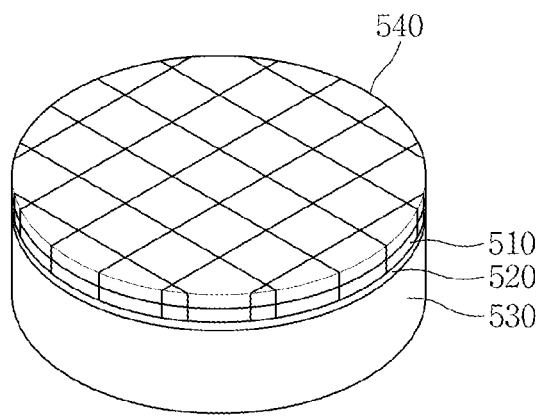
FIG. 17 is an isometric view of a fifth operation for manufacturing a sensed-data processor in accordance with embodiments of the inventive concept.

FIG. 17 is an isometric view of a fifth process step for manufacturing the sensed-data processor in accordance with embodiments of the inventive concept.

Referring to FIG. 17, in the fifth step, the device wafer 510 is diced to separate the plurality of chips connected thereon into individual chips. The dicing of the device wafer 510 may include cutting the strained layer 540 and the device wafer 510 through a dicing pattern.

The dicing of the device wafer 510 may include a method using a dicing blade, a method of irradiating a laser, etc. In the method of radiating the laser, a layered structure 510, 520, 530, and 540 may be fixed to a chuck table. The laser may be radiated onto an upper surface of the strained layer 540 along a dicing pattern. The laser may form a stealthy dicing layer in the device wafer 510. The stealthy dicing layer may form a mesh in the device wafer, which corresponds to the dicing pattern. A sliding unit may apply a tensile force or a shear force to the stealthy dicing layer of the device wafer 510. In this manner, the device wafer 510 may be separated into the plurality of chips corresponding to the dicing pattern.

Figure 18:
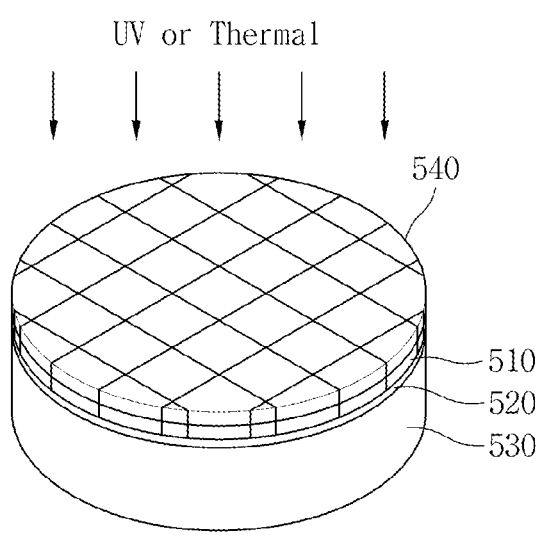
FIG. 18 is an isometric view of a sixth operation for manufacturing a sensed-data processor in accordance with embodiments of the inventive concept.

FIG. 18 is an isometric view of a sixth process step for manufacturing the sensed-data processor in accordance with embodiments of the inventive concept.

Referring to FIG. 18, in the sixth step, the tape 520 may be removed. The tape 520 may be the double-sided tape to be simultaneously attached to the device wafer 510 disposed on an upper surface of the tape 520 and the support substrate 530 disposed on a lower surface of the tape 520. When the tape 520 is removed, the device wafer 510 that has been disposed on the upper surface of the tape 520 that is separated from the support substrate 530 has been disposed on the lower surface of the tape 520.

The tape 520 may be a heat-responsive tape or an ultraviolet-responsive tape. The tape 520 may be melted by the heat or the ultraviolet light. For example, a heater or an ultraviolet radiator may radiate the heat or the ultraviolet light onto the tape 520.

In the sixth step, when the tape 520 is completely melted, the individuated chips and their respective strained layers attached to their rear surfaces may be freely and automatically separated from the substrate 530 and from each other into a plural individual chip units.

Figure 19:
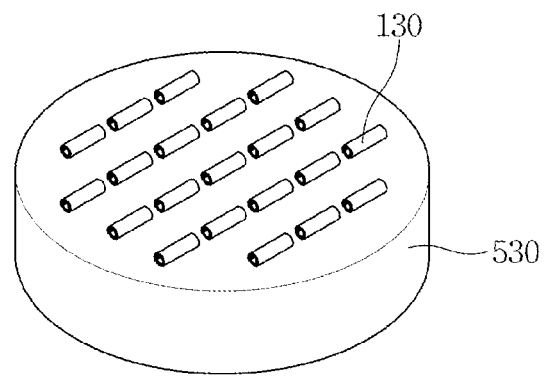
FIG. 19 is an isometric view of a seventh operation for manufacturing a sensed-data processor in accordance with embodiments of the inventive concept.

FIG. 19 is an isometric view of a seventh process step for manufacturing the sensed-data processor in accordance with embodiments of the inventive concept.

Referring to FIG. 19, in the seventh step, the manufacture of the rolled up, generally cylindrical circuit of sensed-data processor 130 may be automatically completed. The sensed-data processor 130 may include a combined structure of the chip and the strained layer attached to the rear surface of the chip. The chip may have a thickness of about 3 µm to 10 µm, so that the chip may be easily bendable or rollable. The strained layer may shrink or expand. The amount of the shrinkage or expansion of the strained layer may be controlled based on a material, a thickness, and/or a modulus of elasticity, etc., thereof. In the sixth step, when the tape 520 is completely melted, the chip and the strained layer automatically are separated from the previously adjacent upper surface of the tape 520. The sensed-data processor 130 may automatically roll and curl into a generally cylindrical shape by the shrinkage or expansion of the strained layer without the need to apply any external force. The sensed-data processor 130 may be rolled in any suitable number of turns such as one and a half turn, two turns, etc., based on the thickness of the chip, the material of the strained layer, the thickness of the strained layer, etc. Alternatively, the sensed-data processor 130 may be rolled into a generally cylindrical shape by the application of an external force. Automatic and/or external assistance force means may be used to roll sensed-data processor 130 in its intended generally cylindrical shape.

The rolled up sensed-data processor 130 may be individually used as an end product, e.g. by itself or within a body-implantable tube 110.

Figure 20:
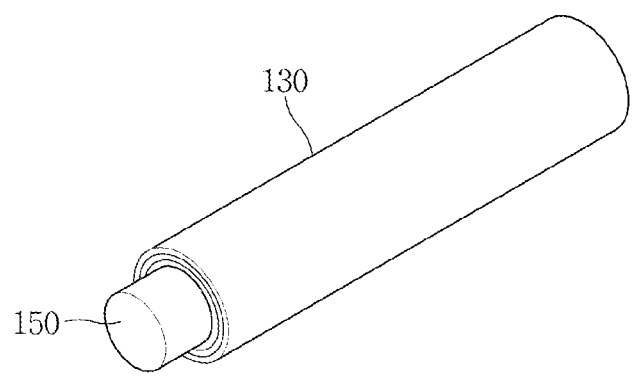
FIG. 20 is an isometric view of an eighth operation for manufacturing a sensed-data processor in accordance with embodiments of the inventive concept.

FIG. 20 is an isometric view of an eighth process step for manufacturing the sensed-data processor in accordance with embodiments of the inventive concept.

Referring to FIG. 20, in the eighth step, the sensed-data processor 130 may be coupled to an auxiliary element 150.

The auxiliary element 150 may be added to perform an additional operation that is not performed by the sensed-data processor 130 or to add a required function to the body-implantable packages for processing the sensed-data.

When the sensed-data processor 130 does not include a power generation part, the auxiliary element 150 may include a battery. When the auxiliary element 150 includes the battery and the battery is depleted, the sensed-data processor 130 may cease operation. Even though the sensed-data processor 130 includes the power generation part, the auxiliary element 150 may also include the battery as a spare power source.

When the sensed-data processor 130 does not include a sensor, the auxiliary element 150 may include the sensor. The sensor may include a blood pressure sensor, a heart rate sensor, a camera, a thermometer, a composition detection sensor, etc.

When the sensed-data processor 130 does not include a wireless communication circuit, the auxiliary element 150 may include the wireless communication circuit.

The auxiliary element 150 may have a combined structure including two or more of the battery, the sensor, and the wireless communication circuit, etc.

The auxiliary element 150 may include a drug tube.

Figure 21:
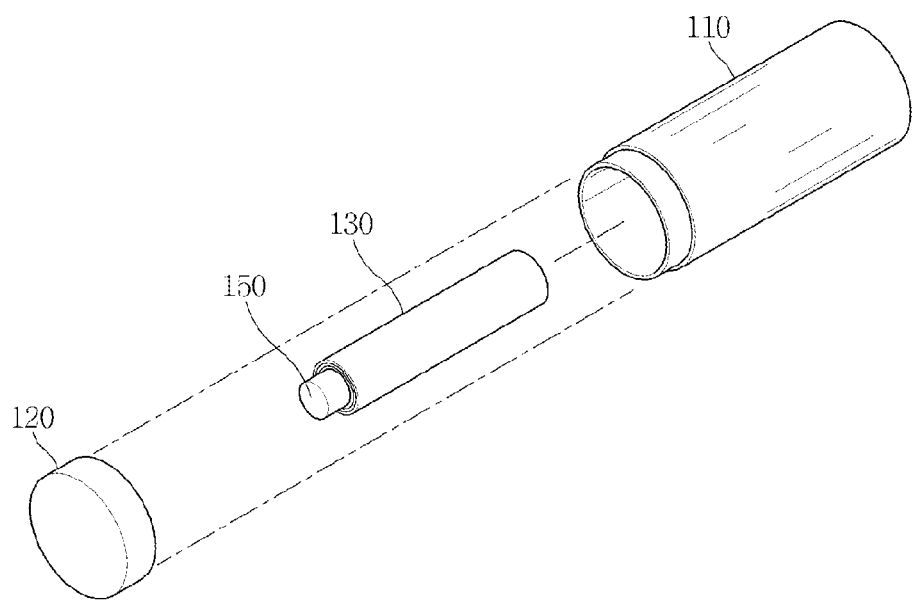
FIG. 21 is an isometric view of a ninth operation for manufacturing a sensed-data processor in accordance with embodiments of the inventive concept.

FIG. 21 is an isometric view of a ninth process step for manufacturing the sensed-data processor in accordance with embodiments of the inventive concept.

Referring to FIG. 21, the sensed-data processor 130 may be coupled to the auxiliary element 150 to be inserted into the tube 110.

The sensed-data processor 130 may be rolled up to have a cylindrical shape. The sensed-data processor 130 may be inserted into the tube 110 having a cylindrical shape.

When the diameter of the sensed-data processor 130 is smaller than the internal diameter of the tube 110, the sensed-data processor 130 may drift in the tube 110. When the operation of the sensed-data processor 130 is not adversely affected by a drifting condition of the sensed-data processor 130 in the tube 110, the sensed-data processor 130 may be inserted into the tube 110 despite the drifting condition.

When the function of the sensed-data processor 130 is adversely affected by the drifting condition of the sensed-data processor 130 in the tube 110, a fixing part may be disposed inside the tube 110. The fixing part may include a non-conductive material such as a thermosetting material, for example, a thermosetting epoxy, silicone, etc.

When the diameter of the sensed-data processor 130 is greater than the internal diameter of the tube 110, the generally cylindrically shaped sensed-data processor 130 having a generally circular cross section may be elastically shrunk in diameter toward a central axis thereof. Thus, the outer surface of the sensed-data processor 130 would come into contact with the inner surface of the tube as the sensed-data processor 130 is inserted into the tube 110.

Figure 22:
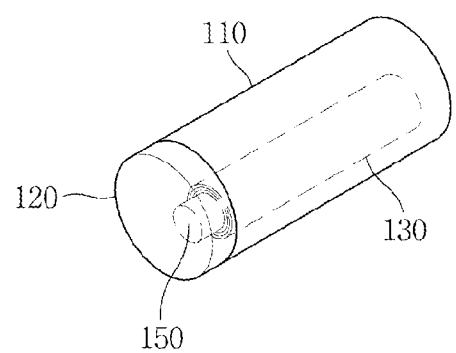
FIG. 22 is an isometric view of a tenth operation for manufacturing a sensed-data processor in accordance with embodiments of the inventive concept.

FIG. 22 is an isometric view of a tenth process step for manufacturing the sensed-data processor in accordance with embodiments of the inventive concept.

Referring to FIG. 22, in the tenth step, manufacturing process for the body-implantable package for processing the sensed-data, which includes the sensed-data processor 130, is completed.

The body-implantable package for processing the sensed-data may be used for a medical sensing apparatus that performs predetermined functions such as sensing the blood pressure, sensing the heart rate, detecting a predetermined composition, detecting an image of digestive organs, etc.

The body-implantable package for processing the sensed-data may be configured to perform at least two functions including the sensing of the blood pressure, the sensing of the heart rate, the detecting the predetermined composition, the detecting the image of the digestive organs, etc.

The method for manufacturing the sensed-data processor shown in FIGS. 13 to 22 is an example of a method of manufacturing the sensed-data processor shown in FIGS. 10 and 12. The sensed-data processor shown in FIGS. 10 and 12 includes the chip combined with the strained layer on the surface of the chip on which the circuit layer of the chip is formed.

In FIGS. 9 and 11, the sensed-data processor includes the chip and the strained layer affixed to the rear surface of the chip. In the method of manufacturing the sensed-data processor of FIGS. 9 and 11, after the grinding of the rear surface of the device wafer 510 to decrease the thickness of the device wafer 510, the first process step of FIG. 13 is performed. Then, the device wafer 510 is combined with the support substrate 530 through the tape 520 as shown in FIG. 13. Then, the operations shown in FIGS. 14 and 15 may be omitted, and the steps illustrated in FIGS. 16-22 may be performed.

According to the embodiments of the inventive concept, the body-implantable package for processing the sensed-data that includes a sensed-data processor for processing the sensed-data is implanted into the human body. However, the body-implantable package for processing the sensed-data that include the sensed-data processor for processing the sensed-data alternatively may be implanted into an animal body.

According to the inventive concept, the sensed-data processor may be rolled into a generally cylindrical shape by expansion or shrinkage thereof to enable the same to be easily inserted into a cylindrical tube.

Also, the expansion ratio or shrinkage ratio of the strained layer is controlled so that the sensed-data processor may be rolled in one or more turns tightly into a generally cylindrical shape. Thus, the volume of the sensed-data processor is variably controllable as desired.

In addition, the volume of the tube may be decreased by the shrinkage of the volume of the sensed-data processor, so that the entire volume of the sensed-data processor and the package containing it may be decreased to be less intrusively body-implanted.

Furthermore, other technical effects may be derived from the embodiments of the inventive concept. However, the other technical effects that are not illustrated will be easily derived or induced by those skilled in the art. The foregoing is illustrative of embodiments and is not to be construed as limiting thereof. Although a few embodiments have been described, those skilled in the art will readily appreciate that many modifications are possible in embodiments without materially departing from the novel teachings and advantages. Accordingly, all such modifications are intended to be included within the scope of this inventive concept as defined in the claims. In the claims, means-plus-function clauses are intended to cover the structures described herein as performing the recited function, and not only structural equivalents but also equivalent structures. Therefore, it is to be understood that the foregoing is illustrative of various embodiments and is not to be construed as limited to the specific embodiments disclosed, and that modifications to the disclosed embodiments, as well as other embodiments, are intended to be included within the scope of the appended claims.

What is claimed is:

1. A sensed-data processor comprising:
 a flex circuit with a strained layer affixed to a surface thereof, wherein the strained layer causes the flex circuit to produce a laminar flex circuit structure, the flex circuit comprising a bio-sensor part, a data processor part coupled with the bio-sensor part, and a wireless communication part coupled with the data processor part,
 wherein the laminar flex circuit structure is rolled in one or more turns, and
 wherein the flex circuit has a thickness of about 3 to about 10 μm.

2. The sensed-data processor according to claim 1, wherein the strained layer is affixed to a circuit layer of the flex circuit.

3. The sensed-data processor according to claim 1, wherein the strained layer is affixed to a rear surface of the flex circuit.

4. The sensed-data processor according to claim 1, wherein the strained layer comprises at least one compound selected from SiO, SiOH, SiN, SiON, SiHN, AlO, or ZrO, and
 wherein the strained layer has a thickness of about 1 to about 3 μm.

5. The sensed-data processor according to claim 1, wherein the strained layer comprises Si, and
 wherein the strained layer has a thickness of about 3 to about 10 μm.

6. The sensed-data processor according to claim 1, wherein the flex circuit comprises a system on chip (SoC).

7. The sensed-data processor according to claim 1, wherein the flex circuit further comprises a power generation part, a control part and a memory part.

8. A system for processing sensed-data within a body, the system comprising:
- a body-implantable package for processing sensed-data, the body-implantable package comprising:
  - a flexible circuit layer,
  - a strained layer affixed to the flexible circuit layer,
  - the strained layer causing the flexible circuit layer to be rolled into a curl-biased circuit layer having one or more turns,
  - the curl-biased circuit layer including a circuit comprising a sensor means, a power generation means, a control means, and a wireless communication means, and
  - a close-able tube sealingly containing the curl-biased circuit layer; and
- a device configured to be external to a package-implanted body, the device configured to receive processed-sensed data transmitted by the wireless communication means,
- wherein the flexible circuit layer and the strained layer are rolled automatically as a result of manufacturing process steps comprising:
- dicing a wafer bearing the curl-biased circuit layer and the strained layer into individuated chips; and
- melting an adhesive layer between the wafer and a substrate to separate the wafer from the substrate,
- wherein the dicing and melting steps release the curl-biased circuit layer and the strained layer as a unit to roll in one or more turns into a generally cylindrical shape.

9. The system of claim 8, wherein
wherein the body-implantable package comprises a plurality of packages configured to be implanted within the same body.

10. The system of claim 9, further comprising:
a repeater operatively coupled between the body-implantable package in plural and the device.

* * * * *